(12) United States Patent
Thompson

(10) Patent No.: US 8,869,801 B1
(45) Date of Patent: Oct. 28, 2014

(54) CUSHIONED RESTRAINT ASSEMBLY

(76) Inventor: Joseph S. Thompson, Fort Lauderdale, FL (US)

(*) Notice: Subject to any disclaimer, the term of this patent is extended or adjusted under 35 U.S.C. 154(b) by 49 days.

(21) Appl. No.: 13/557,624

(22) Filed: Jul. 25, 2012

(51) Int. Cl.
*A61F 5/37* (2006.01)
*A61F 5/00* (2006.01)

(52) U.S. Cl.
USPC .......................................... 128/869; 602/21

(58) Field of Classification Search
USPC .................. 128/869, DIG. 20, 878–879, 846, 128/875–876; 24/196; 602/5, 13, 23, 602/20–21; 606/201–203, 240–241; 5/623–624, 646–647, 648–650, 661
See application file for complete search history.

(56) References Cited

U.S. PATENT DOCUMENTS

| | | | | |
|---|---|---|---|---|
| 1,596,792 A | * | 8/1926 | Barry et al. | 128/878 |
| 3,581,740 A | | 6/1971 | Sherbourne | |
| 3,741,207 A | | 6/1973 | Fuson | |
| 3,906,937 A | * | 9/1975 | Aronson | 600/493 |
| 4,142,522 A | * | 3/1979 | Hill | 128/881 |
| 5,123,153 A | * | 6/1992 | Krauss | 24/196 |
| 5,309,573 A | | 5/1994 | Solar et al. | |
| D354,137 S | | 1/1995 | Neal | |
| 5,472,000 A | * | 12/1995 | Olsen | 128/878 |
| 5,718,669 A | * | 2/1998 | Marble | 602/5 |
| 2008/0077151 A1 | * | 3/2008 | Kring | 606/88 |
| 2010/0218776 A1 | | 9/2010 | Orihashi et al. | |

* cited by examiner

*Primary Examiner* — Ophelia A Hawthorne

(57) ABSTRACT

A cushioned restraint assembly secures a limb comfortably to a structure. The assembly includes an elongated cuff configured for encircling a limb. A band is coupled to and extends along the cuff. The band is configured for securing the cuff around the limb. A strap is coupled to and extends from the cuff. The strap is configured for coupling to a structure. A cushion is coupled to an interior face of the cuff whereby the cushion is configured for positioning between the cuff and the limb.

7 Claims, 4 Drawing Sheets

US 8,869,801 B1

CUSHIONED RESTRAINT ASSEMBLY

BACKGROUND OF THE DISCLOSURE

Field of the Disclosure

The disclosure relates to restraint devices and more particularly pertains to a new restraint device for cushioning limbs held secure by the restraint device.

SUMMARY OF THE DISCLOSURE

An embodiment of the disclosure meets the needs presented above by generally comprising an elongated cuff configured for encircling a limb. A band is coupled to and extends along the cuff. The band is configured for securing the cuff around the limb. A strap is coupled to and extends from the cuff. The strap is configured for coupling to a structure. A cushion is coupled to an interior face of the cuff whereby the cushion is configured for positioning between the cuff and the limb.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
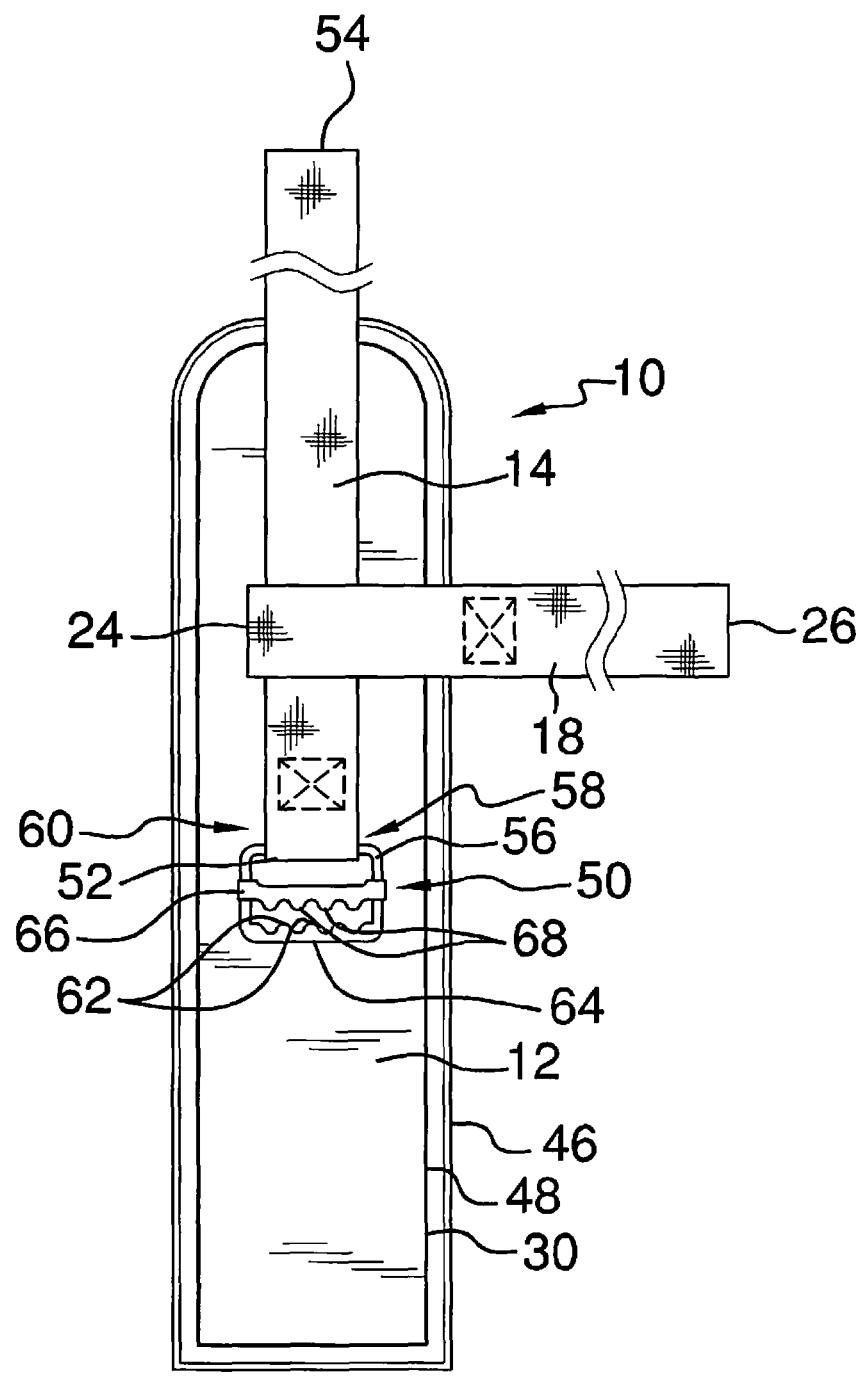
FIG. 1 is an in-use perspective view of a cushioned restraint assembly according to an embodiment of the disclosure.
Figure 2:
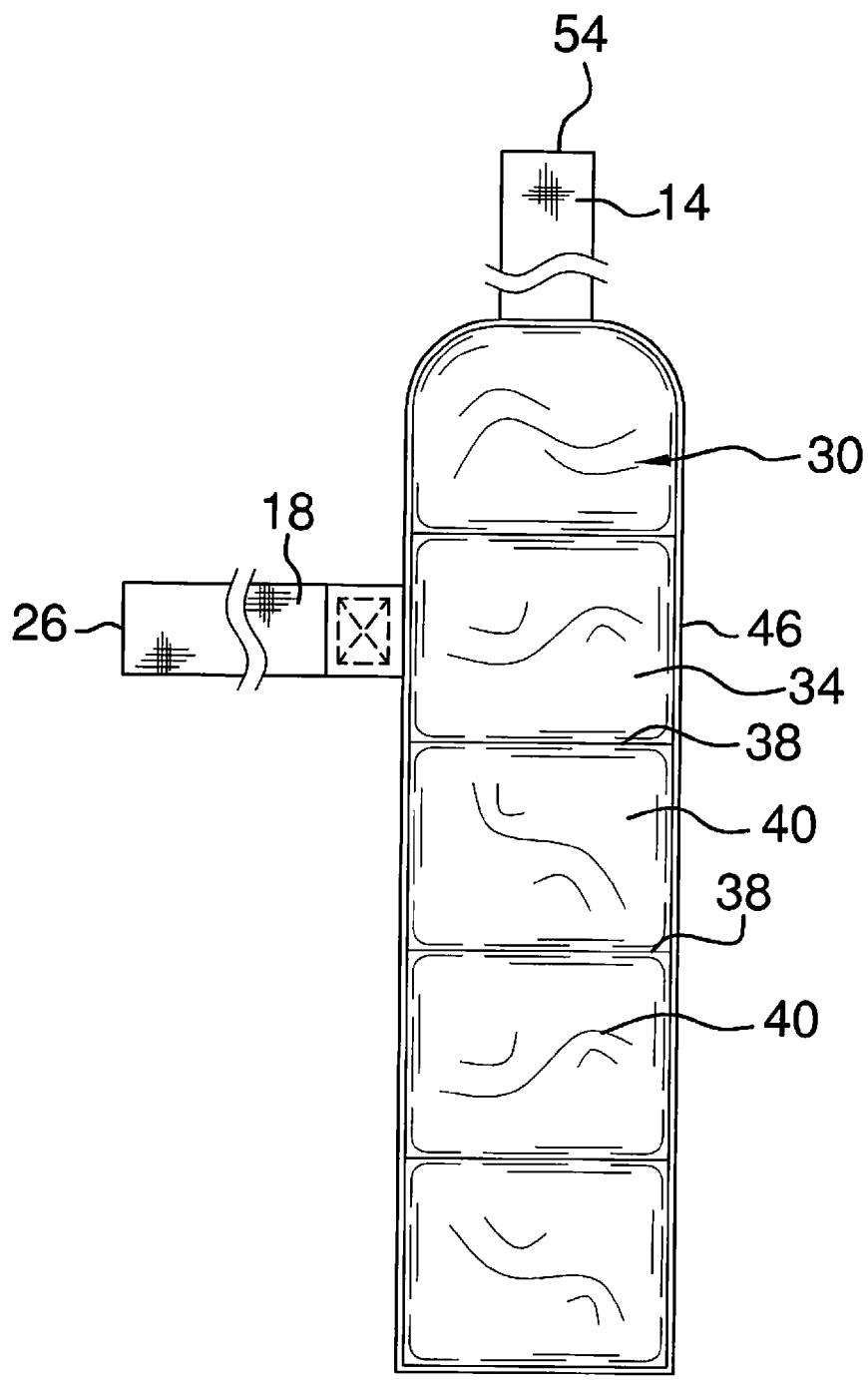
FIG. 2 is a top view of an embodiment of the disclosure.
Figure 3:
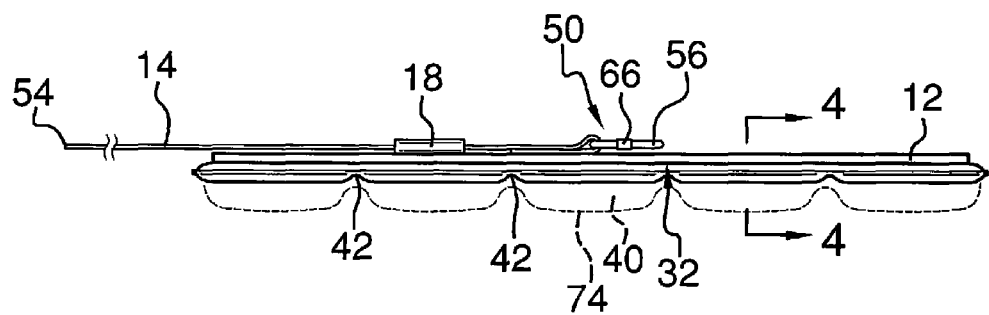
FIG. 3 is a bottom view of an embodiment of the disclosure.
Figure 4:
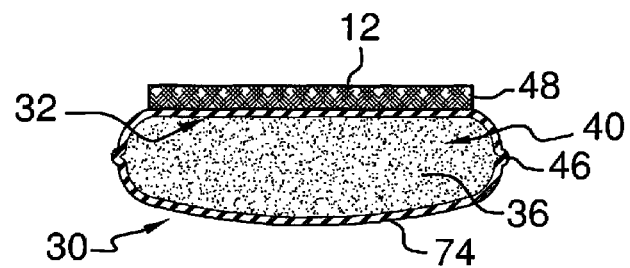
FIG. 4 is a side view of an embodiment of the disclosure.
Figure 5:
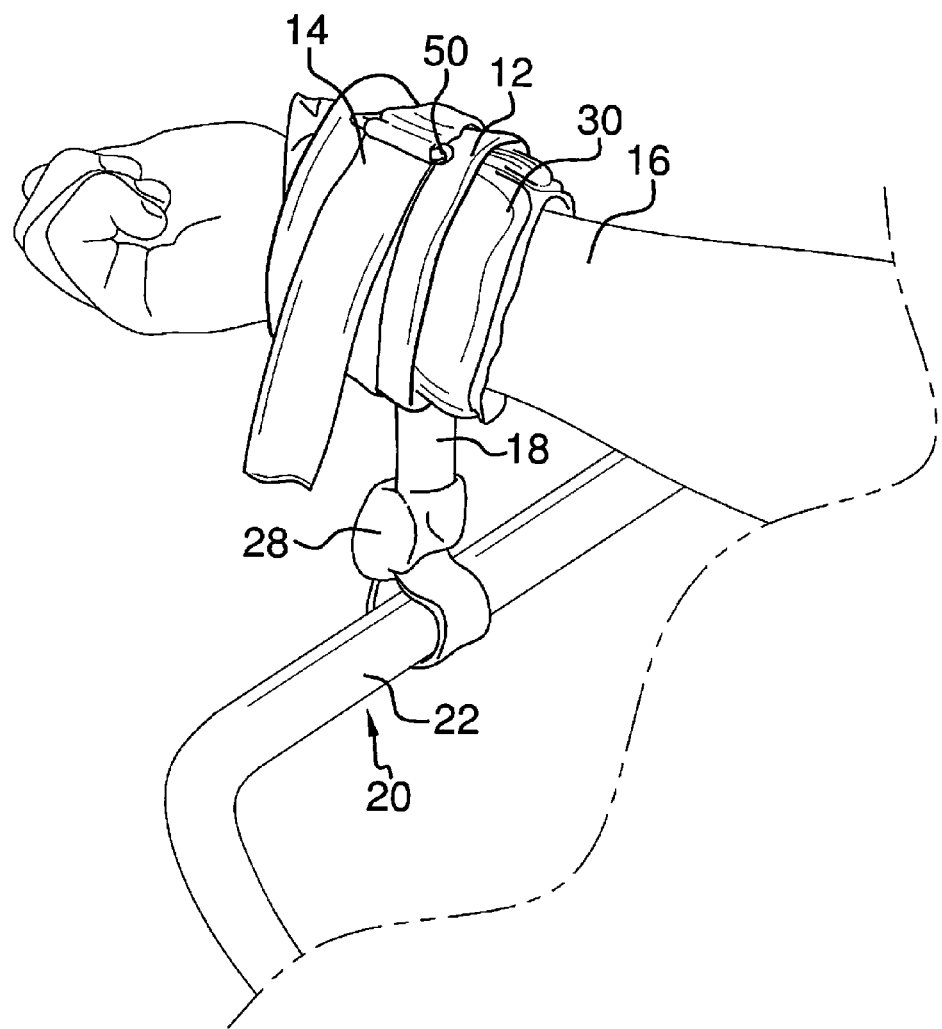
FIG. 5 is a cross-sectional view of an embodiment of the disclosure taken along line 5-5 of FIG. 4.

With reference now to the drawings, and in particular to FIGS. 1 through 5 thereof, a new restraint device embodying the principles and concepts of an embodiment of the disclosure and generally designated by the reference numeral 10 will be described.

As best illustrated in FIGS. 1 through 5, the cushioned restraint assembly 10 generally comprises an elongated flexible cuff 12 configured for encircling a limb 16 such as an arm or leg. A band 14 coupled to and extends along a longitudinal axis of the cuff 12. The band 14 has a length greater than a length of the cuff 12. The band 14 is configured for securing the cuff 12 around the limb 16. A strap 18 is coupled to and extends transversely from the cuff 12. The strap 18 is configured for coupling to a structure 20 such as a bed rail 22. The strap 18 may have a first end 24 coupled to the band 14. The strap 18 has a second end 26 extending away from the cuff 12 configured for coupling to the structure 20 by tying the strap 18 into a knot 28.

A cushion 30 is coupled to an interior face 32 of the cuff 12 whereby the cushion 30 is configured for positioning between the cuff 12 and the limb 16. The cushion 30 is a bladder 34 filled with a cushioning material 36. The cushioning material 36 may be air or gel. The bladder 34 has a plurality of spaced walls 38 defining a plurality of chambers 40. Indentations 42 are formed between the chambers 40 and extending towards the cuff 12 to facilitate bending of the bladder 34 around the limb 16. Each of the chambers 40 is filled with the cushioning material 36. An outer perimeter edge 46 of the cushion 30 is laterally offset from a peripheral edge 48 of the cuff 12 whereby the cushion 30 covers an entirety of the interior face 32 of the cuff 12. The bladder 34 is filled such that each chamber 40 is sufficiently bulbous to prevent the peripheral edge 48 of the cuff 12 from contacting the limb 16. Further, the outer perimeter edge 46 of the bladder 34 may be prevented from contacting the limb 16 by an outwardly facing surface 74 of each chamber 40 being rounded when the chamber 40 is filled with the cushioning material 36.

A buckle 50 is coupled to a first end 52 of the band 14. A second end 54 of the band 14 is selectively couplable to the buckle 50 such that the band 14 is securable around the cuff 12. The buckle 50 may have a loop 56. A first elongated side 58 of the loop 56 is coupled to the band 14. The buckle 50 may be positioned proximate a center 60 of the cuff 12 to prevent the buckle 50 from contacting the limb 16. A plurality of teeth 62 extend from a second elongated side 64 of the loop 56 towards the first elongated side 58 of the loop 56. A sliding jaw 66 of the buckle 50 is coupled to the loop 56. The jaw 66 has a plurality of complimentary teeth 68 extending towards and interlocking with the teeth 62 on the first side 58 of the loop 56. Thus, the buckle 50 prevents loosening of the band 14 from around the cuff 12 when the band 14 is engaged to the buckle 50 around the jaw 66 and further extending between the first side 58 of the loop 56 and the jaw 66.

In use, the cuff 12 is positioned around the limb 16. The band 14 is secured around the cuff 12 by the buckle 50 holding the cuff 12 on the limb 16. The strap 18 is secured to the structure 20. Thus, the assembly 10 provides secure comfortable coupling of the limb 16 to the structure 20 as may be needed in a hospital setting or similar situation.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:
1. A cushioned restraint assembly for securing a limb to a structure, the assembly comprising:
   an elongated cuff configured for encircling the limb;
   a band coupled to and extending along a longitudinal axis of said cuff, said band being configured for securing said cuff around the limb wherein a first end of said cuff is selectively coupled to a second end of said cuff;

a strap coupled to and extending transversely relative to the longitudinal axis of said cuff, said strap being configured for coupling to the structure;

a cushion coupled to an interior face of said cuff whereby said cushion is configured for positioning between said cuff and the limb, said cushion being a bladder filled with a cushioning material, said bladder having a plurality of spaced walls defining a plurality of chambers, each of said chambers being filled with said cushioning material; and a plurality of indentations, each of an associated one of said indentations being formed between adjacently positioned said chambers, each of said indentations extending towards said cuff wherein said indentations are configured to facilitate bending of said bladder around the limb.

2. The assembly of claim 1, further including a buckle coupled to a first end of said band, a second end of said band being selectively couplable to said buckle such that said band is securable around said cuff.

3. The assembly of claim 2, further comprising:

said buckle having a loop, a first elongated side of said loop being coupled to said band;

a plurality of teeth extending from a second elongated side of said loop towards said first elongated side of said loop; and a sliding jaw of said buckle being coupled to said loop, said jaw having a plurality of complimentary teeth extending towards and interlocking with said teeth on said first side of said loop whereby said buckle prevents loosening of said band from around said cuff when said band is engaged to said buckle around said jaw and further extending between said first side of said loop and said jaw.

4. The assembly of claim 3, further including said buckle being positioned proximate a center of said cuff.

5. The assembly of claim 1, further including said strap having a first end coupled to said band, said strap having a second end configured for coupling to the structure.

6. The assembly of claim 1, further including an outer perimeter edge of said cushion being laterally offset from a peripheral edge of said cuff whereby said cushion covers an entirety of said interior face of said cuff.

7. A cushioned restraint assembly for securing a limb to a structure, the assembly comprising:

an elongated cuff configured for encircling the limb;

a band coupled to and extending along a longitudinal axis of said cuff, said band being configured for securing said cuff around the limb wherein a first end of said cuff is selectively coupled to a second end of said cuff;

a strap coupled to and extending transversely relative to the longitudinal axis of said cuff, said strap being configured for coupling to the structure, said strap having a first end coupled to said band, said strap having a second end configured for coupling to the structure;

a cushion coupled to an interior face of said cuff whereby said cushion is configured for positioning between said cuff and the limb, said cushion being a bladder filled with a cushioning material, said bladder having a plurality of spaced walls defining a plurality of chambers, each of said chambers being filled with said cushioning material;

a plurality of indentations, each of an associated one of said indentations being formed between adjacently positioned said chambers, each of said indentations extending towards said cuff wherein said indentations are configured to facilitate bending of said bladder around the limb;

an outer perimeter edge of said cushion being laterally offset from a peripheral edge of said cuff whereby said cushion covers an entirety of a lower surface of said cuff;

a buckle coupled to a first end of said band, a second end of said band being selectively couplable to said buckle such that said band is securable around said cuff, said buckle having a loop, a first elongated side of said loop being coupled to said band, said buckle being positioned proximate a center of said cuff;

a plurality of teeth extending from a second elongated side of said loop towards said first elongated side of said loop; and a sliding jaw of said buckle being coupled to said loop, said jaw having a plurality of complimentary teeth extending towards and interlocking with said teeth on said first side of said loop whereby said buckle prevents loosening of said band from around said cuff when said band is engaged to said buckle around said jaw and further extending between said first side of said loop and said jaw.

* * * * *